United States Patent [19]

Menapace

[11] 4,204,081
[45] May 20, 1980

[54] SELECTIVE HYDROGENATION OF CYCLOPENTADIENE TO FORM CYCLOPENTENE

[75] Inventor: Henry R. Menapace, Stow, Ohio

[73] Assignee: The Goodyear Tire & Rubber Company, Akron, Ohio

[21] Appl. No.: 938,159

[22] Filed: Aug. 30, 1978

[51] Int. Cl.² .................... C07C 5/06; C07C 5/16; C07C 13/12
[52] U.S. Cl. .................... 585/274; 585/271; 585/272; 585/277
[58] Field of Search .................... 260/666 A, 667; 585/273, 274, 277, 272, 271

[56] References Cited

U.S. PATENT DOCUMENTS

| | | | |
|---|---|---|---|
| 3,022,359 | 2/1962 | Wiese et al. | 260/666 A |
| 3,360,577 | 12/1967 | Pickles | 260/666 A |
| 3,937,745 | 2/1976 | Wideman et al. | 260/666 A |
| 4,112,007 | 5/1978 | Sanfilippo et al. | 260/666 A |

*Primary Examiner*—Veronica O'Keefe
*Attorney, Agent, or Firm*—J. Y. Clowney

[57] ABSTRACT

There is disclosed a process for the preparation of cyclopentene which comprises selectively hydrogenating cyclopentadiene in a liquid phase by contacting cyclopentadiene with hydrogen in the presence of a hydrogenation catalyst comprising (1) a soluble nickel compound, (2) an organoaluminum compound or a lithium alkyl compound, and (3) at least one cocatalyst compound selected from the group consisting of $H_2O$; $NH_3$; ROH where R is an alkyl or a halogenated alkyl radical containing from 1 to 20 carbon atoms;

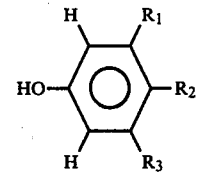

where $R_1$, $R_2$ and $R_3$ may be hydrogen, or an alkyl radical containing from 1 to 6 carbon atoms;

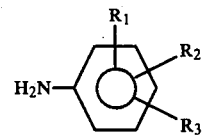

where $R_1$, $R_2$ and $R_3$ may be hydrogen or halogen, or an alkyl radical containing from 1 to 6 carbon atoms; $R_1O$ $R_2$ wherein $R_1$ and $R_2$ may be the same or different alkyl radicals containing from 1 to 6 carbon atoms; and

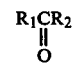

wherein $R_1$ may be alkyl or an aromatic radical containing from 1 to 8 carbon atoms and $R_2$ may be hydrogen or an alkyl or aromatic hydrocarbon radical containing from 1 to 8 carbon atoms.

5 Claims, No Drawings

SELECTIVE HYDROGENATION OF CYCLOPENTADIENE TO FORM CYCLOPENTENE

BACKGROUND OF THE INVENTION

This invention is directed to the selective hydrogenation of dienes to monoolefins, particularly to the selective hydrogenation of cyclopentadiene to cyclopentene. More specifically, it is directed to a process wherein cyclopentene is prepared which comprises selectively hydrogenating cyclopentadiene in a liquid phase by contacting cyclopentadiene with hydrogen in the presence of a hydrogenation catalyst comprising (1) a soluble nickel compound, (2) an aluminum trialkyl compound or a lithium alkyl compound, and (3) at least one cocatalyst compound selected from the group consisting of $H_2O$; $NH_3$; ROH where R is an alkyl or a halogenated alkyl radical containing from 1 to 20 carbon atoms;

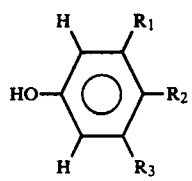

where $R_1$, $R_2$ and $R_3$ may be hydrogen, or an alkyl radical containing from 1 to 6 carbon atoms;

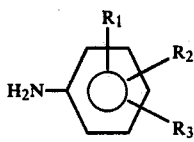

where $R_1$, $R_2$ and $R_3$ may be hydrogen or halogen, or an alkyl radical containing from 1 to 6 carbon atoms; $R_1OR_2$ wherein $R_1$ and $R_2$ may be the same or different alkyl radicals containing from 1 to 6 carbon atoms; and

wherein $R_1$ may be alkyl or an aromatic radical containing from 1 to 8 carbon atoms and $R_2$ may be hydrogen or an alkyl or aromatic hydrocarbon radical containing from 1 to 8 carbon atoms.

At the present time, substantial amounts of cyclopentadiene, usually as dicyclopentadiene, are available as a byproduct from the steam cracking of naphtha to produce primarily ethylene. Cyclopentene has been found to be useful as a monomer for the formation of general purpose elastomers by ring opening polymerization of cyclopentene. Therefore, it is desirable to convert a portion of the excess cyclopentadiene available into a more valuable raw material, such as cyclopentene.

The hydrogenation of cyclopentadiene to cyclopentene is not new. For instance, in U.S. Pat. No. 2,360,555, issued Oct. 17, 1944, there is disclosed a selective hydrogenation of one of the two conjugated double bonds of a cyclic diolefin to produce the corresponding cyclic monoolefin which is accomplished by conducting the hydrogenation in the liquid phase in the presence of an active hydrogenation catalyst, under moderate hydrogen pressure, such as 2 to 5 atmospheres absolute, and at relatively low temperatures, such as from 0° to 40° C. and even up to 100° C., using substantially less than the stoichiometric amount of hydrogen theoretically required to completely reduce the cyclic diene to the corresponding cyclic monoolefin. The catalyst therein disclosed is a pyrophoric nickel metal catalyst, such as Raney nickel.

In U.S. Pat. No. 3,819,734, issued July 25, 1974, there is disclosed the hydrogenation of cyclopentadiene to cyclopentene by bringing cyclopentadiene into contact with a catalyst consisting essentially of (1) nickel, on a magnesium or zinc oxalate support, (2) a ligand selected from the group consisting of trimethyl phosphine, triethyl phosphine, methyl ethyl propyl phosphine, trimethyl phosphite, triethyl phosphite, tributyl phosphite, triphenyl phosphite, etc., while in the presence of hydrogen, at temperatures from 0° C. and at pressures from 0 to 1000 pounds per square inch gauge.

In U.S. Pat. No. 3,994,986, issued Nov. 30, 1976, there is disclosed the preparation of cyclopentene from cyclopentadiene by hydrogenating cyclopentene with hydrogen gas at a ratio of 1 to 1.5 moles of hydrogen per mole of cyclopentadiene in the presence of a palladium catalyst on a carrier. Also, see U.S. Pat. No. 4,108,911, issued Aug. 22, 1978.

Also, in U.S. Pat. No. 3,857,894, issued Dec. 31, 1974, there is disclosed the hydrogenation of cyclopentadiene to cyclopentene in the presence of a palladium catalyst and a small amount of an aqueous solution of zinc salt having a water/zinc ratio of at least 1/1 by weight.

Also, see German Patent No. 2,327,230.

The cyclopentadiene employed in the formation of cyclopentene by hydrogenation is usually obtained by depolymerizing or cracking dicyclopentadiene. In order to obtain cyclopentadiene for the hydrogenation of this invention, the depolymerization of dicyclopentadiene is accomplished by heating the dimer at a temperature above 150° C. under atmospheric pressure in a conventional cracking apparatus. The depolymerized material should be hydrogenated without substantial delay because it is also known that redimerization will occur upon standing.

SUMMARY OF THE INVENTION

According to the invention, cyclopentadiene can be selectively hydrogenated to cyclopentene in the liquid phase by contacting cyclopentadiene with hydrogen in the presence of a catalyst comprising (1) a soluble nickel compound, (2) an aluminum trialkyl compound or a lithium alkyl compound, and (3) at least one cocatalyst compound selected from the group consisting of $H_2O$; $NH_3$; ROH where R is an alkyl or a halogenated alkyl radical containing from 1 to 20 carbon atoms;

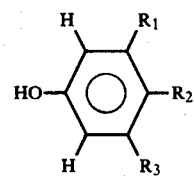

where $R_1$, $R_2$ and $R_3$ may be hydrogen, or an alkyl radical containing from 1 to 6 carbon atoms;

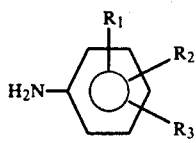

where $R_1$, $R_2$ and $R_3$ may be hydrogen or halogen, or an alkyl radical containing from 1 to 6 carbon atoms; $R_1O R_2$ wherein $R_1$ and $R_2$ may be the same or different alkyl radicals containing from 1 to 6 carbon atoms; and

wherein $R_1$ may be alkyl or an aromatic radical containing from 1 to 8 carbon atoms and $R_2$ may be hydrogen or an alkyl or aromatic hydrocarbon radical containing from 1 to 8 carbon atoms.

DETAILED DESCRIPTION OF THE INVENTION

The temperature at which the cyclopentadiene may be hydrogenated in accordance with the present invention may range from about 0° C. to about 250° C. with about 20° to about 100° C. being more preferred and 30° to 80° C. being most preferred.

Excessively high temperatures tend to cause the cyclopentadiene to form certain undesirable side reactions rather than cyclopentene. Generally speaking, both the temperature and pressure of the hydrogen employed should be kept as low as possible consistent with reasonable reaction rates of hydrogenation.

While no upper limit was determined as far as the hydrogen pressure employed is concerned, the higher the pressure, the faster rates of hydrogenation can be employed. It has been determined, however, that satisfactory results can be obtained when the hydrogen pressure ranges from about 50 to about 600 pounds per square inch gauge or about 3.51 to about 52.18 kilograms per square centimeters.

A variety of inert, aromatic and aliphatic solvents may be employed as the reaction medium. Almost any aromatic or aliphatic hydrocarbon may be employed so long as the catalyst components are soluble in said solvent and the cyclopentadiene reactant is, likewise, soluble in said solvent. Examples of aliphatic solvents are heptane, octane, cyclopentane and the like. Typical examples of such inert aromatic solvents are benzene, toluene, xylene, and the like.

The molar ratio of the catalyst components employed in the process of this invention may vary widely. The preferred molar ratio of the particular cocatalyst compound to the soluble nickel compound may vary from about 1/1 to about 4/1 with a molar ratio of cocatalyst compound/Ni from 1.5/1 to 3/1 being more preferred. The molar ratio of the organoaluminum compound or the lithium alkyl compound to the soluble nickel compound (Al/Ni) (Li/Ni) may vary from about 6/1 to about 12/1, with about 7/1 to 9/1 being more preferred.

The amount of catalyst to the cyclopentadiene hydrogenated has not been found to be critical and may vary widely from a cyclopentadiene/nickel molar ratio of about 100/1 to about 20,000/1 and has been proved to be satisfactory in the performance of the invention. On the other hand, better reaction rates and more economical operating conditions would be to employ a cyclopentadiene/Ni mole ratio of from 5000/1 to about 15,000/1.

The first catalyst component of the catalyst system of this invention is a soluble nickel compound. By the term "soluble" is meant soluble in inert solvents. Thus, any salt or an organic acid containing from about 1 to 20 carbon atoms may be employed. Representative of organo nickel compounds are nickel benzoate, nickel acetate, nickel naphthenate, nickel octanoate, bis(α-furyl dioxime) nickel, nickel palmitate, nickel stearate, nickel acetylacetonate, nickel salicaldehyde, bis(cyclopentadiene)nickel, bis(salicylaldehyde)ethylene diimine nickel, cyclopentadienyl-nickel nitrosyl, bis(π-allyl nickel trifluoroacetate), and nickel tetracarbonyl. The preferred component containing nickel is a nickel salt of a carboxylic acid or an organic complex compound of nickel. The most preferred are 2-ethyl hexanoate, neodecanoate and the napthenate salts of nickel.

The second or (2) component is an organoaluminum compound. By the term "organoaluminum compound" is meant any organoaluminum compound responding to the formula:

in which $R_1$ is selected from the group consisting of alkyl (including cycloalkyl), aryl, alkaryl, arylalkyl, alkoxy and hydrogen; $R_2$ and $R_3$ being selected from the group of alkyl (including cycloalkyl), aryl, alkaryl, and arylalkyl. Representative of the compounds responding to the formula set forth above are: diethylaluminum hydride, di-n-propyl-aluminum hydride, di-n-butylaluminum hydride, diisobutyl-aluminum hydride, diphenylaluminum hydride, di-p-tolyl-aluminum hydride, dibenzylaluminum hydride, phenyl ethylaluminum hydride, phenyl-n-propylaluminum hydride, p-tolyl ethylaluminum hydride, p-tolyl n-propylaluminum hydride, p-tolyl isopropylaluminum hydride, benzyl ethylaluminum hydride, benzyl n-propylaluminum hydride, and benzyl isopropylaluminum hydride and other organoaluminum hydrides. Also, diethylaluminum ethoxide, diisobutylaluminum ethoxide, and dipropylaluminum methoxide. Also included are trimethylaluminum, triethylaluminum, tri-n-propylaluminum, triisopropylaluminum, tri-n-butylaluminum, triisobutylaluminum, tripentylaluminum, trihexylaluminum, tricyclohexylaluminum, trioctylaluminum, triphenylaluminum, tri-p-tolylaluminum, tribenzylaluminum, ethyl diphenylaluminum, ethyl di-p-tolylaluminum, ethyl dibenzylaluminum, diethyl phenyl aluminum, diethyl p-tolyl aluminum, diethyl benzyl aluminum and other triorganoaluminum compounds. The preferred organoaluminum compounds are trialkylaluminums with aluminum triethyl being the most preferred.

The second component is also a lithium alkyl compound. The term lithium alkyl compound is meant to mean that the organo lithium compound corresponds to the formula R-Li in which R is a monovalent hydrocarbon radical with 1 to 20 carbon atoms, especially n-butyllithium, secondary butyllithium, hexyllithium and methyllithium are representative thereof. Of these, butyllithium is the preferred lithium compound.

As has been indicated, the third catalyst (3) component has been referred to as a cocatalyst compound which may be selected from certain oxygen or nitrogen containing compounds. For instance, water (H₂0) is useful as a cocatalyst compound. Anhydrous ammonia(NH₃) or ammonia in mixture with water is useful. For instance, commercial ammonium hydroxide (NH₄OH) may be employed.

The third catalyst component may also be chosen from certain oxygen containing compounds such as those defined by a formula ROH wherein R is an alkyl or halogenated alkyl radical containing from 1 to 20 carbon atoms. Representative examples of this class of compounds are the simple alcohols such as methanol, ethanol, butanol, hexanol, chloroethanol and the like.

The third catalyst component may also be chosen from those compounds represented by the formula

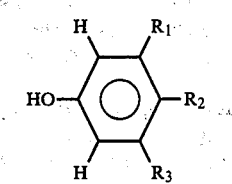

wherein $R_1$, $R_2$ and $R_3$ may be hydrogen or an alkyl radical containing from 1 to 6 carbon atoms. Representative examples of the cocatalysts responding to this formula are phenol, 4-methyl phenol, 3-methyl phenol, 4-butyl phenol and the like.

The third catalyst component may also be represented by the compounds responding to the formula

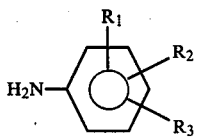

wherein $R_1$, $R_2$ and $R_3$ may be hydrogen, halogen or an alkyl radical containing from 1 to 6 carbon atoms. Representative examples of such materials responding to this formula are aniline, 2-methyl aniline, 4-methyl aniline, 3-chloroaniline, 4-butyl aniline, 3,4-dimethylaniline, 3,4-dichloroaniline and the like.

Another class of compounds which may be employed as cocatalysts in the practice of this invention are those ethers represented by the formula $R_1$—O—$R_2$ wherein $R_1$ and $R_2$ may be the same or different alkyl radicals containing from 1 to 6 carbon atoms. Representative examples of such compounds would be methyl ethyl ether, diethyl ether, dimethyl ether, dibutyl ether and the like.

Still another class of cocatalysts which may be employed in this invention are the compounds responding to the formula

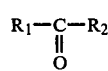

wherein $R_1$ may be an alkyl or aromatic radical of from 1 to 8 carbon atoms and $R_2$ may be hydrogen or an alkyl or aromatic radical containing 1 to 8 carbon atoms. Representative of such compounds are acetaldehyde, acetone, methyl ethyl ketone, acetophenone, 3-pentanone, benzaldehyde and the like.

A preferred group of cocatalyst compounds are those such as water, ammonia, alcohols and phenols or mixtures thereof. Of particular interest are mixtures of water and ammonia.

The catalyst components employed in the hydrogenation catalyst of the invention are soluble in the cyclopentadiene reactant and are soluble in the cyclopentene product. The reactant cyclopentadiene and the product cyclopentene and the catalyst used in this invention are also soluble in a variety of inert solvents, either aromatic or aliphatic, such as pentane, cyclopentane, n-octane, toluene, benzene and the like. Thus, a solvent may be used. If a solvent is used, the cyclopentadiene/solvent volume ratio may vary from 1/1 to 200/1.

The practice of this invention is further illustrated by reference to the following examples which are intended to be representative rather than restrictive of the scope of the invention. Unless otherwise indicated, all parts and percentages are by weight.

EXAMPLE

A series of different catalysts were prepared in which a typical procedure using 1.30 millimoles (mm) of the particular cocatalyst compound were added to 0.65 mm of nickel octanoate as a 0.1 molar solution in toluene to a series of dry 4-oz bottles under nitrogen. After mixing the cocatalyst and the nickel octanoate for 5 minutes at room temperature, 4.55 mm of triethylaluminum as a 2 molar solution a in toluene were added under nitrogen and the mixture stirred for at least two additional minutes.

The thus formed catalyst systems were then employed in an appropriate amount so as to provide 0.1 mm of nickel per mole of cyclopentadiene in a stirred autoclave which was kept near the desired reaction temperature of 40° C. After the catalyst had been mixed with the one mole of cyclopentadiene, hydrogen was admitted to the desired pressure, usually from 350 to 400 psig. The reaction conditions and results are as follows:

| | |
|---|---|
| Cyclopentadiene/nickel mole ratio | 10,000/1 |
| Cocatalyst/nickel mole ratio | 2/1 |
| Al/Ni | 7/1 |
| Hydrogen pressure | 350–400 psig |
| Temperature Range | 39°–42° C. |

Table

| Ex | Compound | Mins of Hydrogenation | % Conv | % CPA | % CPE |
|---|---|---|---|---|---|
| 1 | none | 62 | 96.5 | 8.0 | 88.5 |
| 2 | H₂O | 29 | 97 | 7.1 | 91 |
| 3 | NH₃ | 35.5 | 99 | 11 | 87 |
| 4 | NH₃/H₂O = 0.56/0.74* | 25.5 | 100 | 9.8 | 90 |
| 5 | NH₃/H₂O = 0.38/0.92* | 17 | 100 | 7.7 | 92 |
| 6 | NH₃/H₂O = 0.34/0.96* | 40 | 95 | 8.0 | 92 |
| 7 | NH₃/H₂O = 0.27/1.02* | 23 | 96 | 8.2 | 92 |
| 8 | NH₃/methanol = 0.38/0.92* | 19 | 99.8 | 7.6 | 92 |
| 9 | methanol | 28 | 96 | 5.8 | 92 |
| 10 | ethanol | 23 | 95 | 5.5 | 94.5 |
| 11 | isopropanol | 26.5 | 99 | 6.5 | 93 |
| 12 | n-butanol | 47 | 90 | 6.8 | 93 |
| 13 | tert-butanol | 22 | 98 | 7.2 | 93 |
| 14 | 2-chloroethanol | 23 | 100 | 8.5 | 91.5 |
| 15 | phenol | 32 | 98 | 6.9 | 91 |
| 16 | aniline | 33 | 96 | 8.6 | 91 |
| 17 | 2-methylaniline | 43.5 | 98 | 9.3 | 91 |

Table-continued

| Ex | Compound | Mins of Hydro-genation | % Conv | % CPA | % CPE |
|---|---|---|---|---|---|
| 18 | diethylether | 38 | 95.5 | 9 | 91 |
| 19 | acetone | 40 | 98 | 8.3 | 90 |

% conversion = conversion of cyclopentadiene
% CPA = selectivity to cyclopentane
% CPE = selectivity to cyclopentene
*millimoles of each cocatalyst While certain representative embodiments and details have been shown for the purpose of illustrating the invention, it will be apparent to those skilled in this art that various changes and modifications may be made therein without departing from the spirit or scope of the invention.

What is claimed is:

1. A process for the preparation of cyclopentene which comprises selectively hydrogenating cyclopentadiene in the liquid phase by contacting cyclopentadiene with hydrogen in the presence of a hydrogenation catalyst comprising (1) a soluble nickel compound, (2) an aluminum trialkyl compound or a lithium alkyl and (3) at least one cocatalyst compound selected from the group consisting of $H_2O$; $NH_3$;

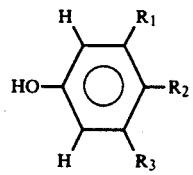

where $R_1$, $R_2$ and $R_3$ may be hydrogen or an alkyl radical containing from 1 to 6 carbon atoms;

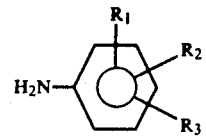

where $R_1$, $R_2$ and $R_3$ may be hydrogen or halogen, or an alkyl radical containing from 1 to 6 carbon atoms; $R_1O$ $R_2$ wherein $R_1$ and $R_2$ may be the same or different alkyl radicals containing from 1 to 6 carbon atoms; and $$\underset{O}{\overset{R_1CR_2}{\|}}$$

wherein $R_1$ may be alkyl or an aromatic radical containing from 1 to 8 carbon atoms and $R_2$ may be hydrogen or an alkyl or aromatic hydrocarbon radical containing from 1 to 8 carbon atoms.

2. A process according to claim 1 in which the mole ratio of the cocatalyst component and the soluble nickel compound may vary from about 1/1 to about 4/1 and the molar ratio of the organoaluminum compound or the lithium alkyl compound to the soluble nickel compound may vary from about 6/1 to about 12/1.

3. The process according to claim 2 in which the soluble nickel compound is nickel octanoate.

4. The process according to claim 2 in which the organoaluminum compound is triethylaluminum.

5. The process according to claim 2 in which the soluble nickel compound is a nickel salt of carboxylic acid and the cocatalyst compound is at least one member selected from the group of ammonia and water.

* * * * *